United States Patent [19]

Bruno

[11] Patent Number: 4,785,126
[45] Date of Patent: Nov. 15, 1988

[54] 1,4-O-METALLATION PROCESS AND COMPOSITION

[75] Inventor: Salvatore A. Bruno, Wilmington, Del.

[73] Assignee: E. I. Du Pont de Nemours and Company, Wilmington, Del.

[21] Appl. No.: 727,813

[22] Filed: Apr. 26, 1985

[51] Int. Cl.[4] ........................... C07F 7/08; C07F 7/10; C07F 7/18; C07F 7/22
[52] U.S. Cl. ......................... 556/423; 556/81; 556/88; 556/89; 556/437; 556/444; 556/446; 556/470; 556/482; 549/214
[58] Field of Search ............... 556/423, 444, 437, 446, 556/470, 482, 81, 88, 89; 549/214

[56] References Cited

U.S. PATENT DOCUMENTS

| | | | |
|---|---|---|---|
| 2,721,873 | 10/1955 | MacKenzie | 260/488.2 |
| 2,917,530 | 12/1959 | Bailey | 260/488.2 |
| 3,527,794 | 9/1970 | Heck | 556/81 X |
| 3,536,745 | 10/1970 | Dear | 556/470 |
| 3,641,077 | 2/1972 | Rochow | 556/81 |
| 3,775,453 | 11/1973 | Mazdiyasni et al. | 556/81 X |
| 3,781,315 | 12/1973 | Pepe et al. | 556/81 |
| 3,856,843 | 12/1974 | Nagai et al. | 556/470 X |
| 3,890,359 | 6/1975 | Chandra | 260/429 |
| 4,064,154 | 12/1977 | Chandra et al. | 260/448.2 |
| 4,332,654 | 6/1982 | Yates | 556/470 X |
| 4,383,120 | 5/1983 | Yates | 556/470 |
| 4,414,376 | 11/1983 | Siedle | 528/15 |
| 4,503,160 | 8/1983 | Williams | 502/158 |

FOREIGN PATENT DOCUMENTS

| | | |
|---|---|---|
| 1044448 | 9/1966 | United Kingdom . |
| 1419769 | 12/1975 | United Kingdom . |
| 1420928 | 1/1976 | United Kingdom . |
| 1421136 | 1/1976 | United Kingdom . |

OTHER PUBLICATIONS

Journal of General Chemistry (USSR), 29:2896–2899 (1959), "The Addition of Silicohydrocarbons to $\alpha,\beta$-Unsaturated Acids and Their Esters", Petrov et al.
Chem. Pharm. Bull. vol. 22, No. 11:2767–2769 (1974), "Hydrosilation of $\alpha,\beta$-Unsaturated Esters", by Yoshii et al.
Journal of American Chemical Society, vol. 79:974–979 (1957), "The Addition of Silicon Hydrides to Olefinic Double Bonds, Part II, The Use of Group VIII Metal Catalysts", Speier et al.
Journal of American Chemical Society, vol. 79:2764–2769 (1957), "Aliphatic Organo-Functional Siloxanes. V. Synthesis of Monomers by Platinum-Catalyzed Addition of Methyldichlorosilane to Unsaturated Esters and Nitriles", Sommer et al.
Tetrahedron Letters, No. 49:5035–5038 (1972), "Selective Reduction of $\alpha,\beta$-Unsaturated Terpene Carbonyl Compounds Using Hydrosilane-Rhodium (I) Complex Combinations", Ojima et al.
Synthesis (1977), pp. 91–110, "O-Silylated Enolates--Versatile Intermediates for Organic Synthesis", Rasmussen.
Synthesis (1983), pp. 1–28, "Silyl Enol Ethers in Synthesis–Part I", Brownbridge.
Organometallic Chemistry Review A, 6 (1970), pp. 355, 382–390.

Primary Examiner—Paul F. Shaver
Attorney, Agent, or Firm—Craig H. Evans

[57] ABSTRACT

This invention resides in a process for production of predominantly a 1,4-O-metallation product of a hydride of silicon, germanium, or tin with an $\alpha,\beta$-unsaturated carbonyl compound. The reaction involved takes place in the presence of a heterogeneous noncomplexed rhodium-containing catalyst. This invention also resides in 1,4-O-metallation compositions having perfluoroalkyl R groups on either side of the C=C bond of an enol ether or on the acetal side of the C=C bond of a ketene acetal.

6 Claims, No Drawings

1,4-O-METALLATION PROCESS AND COMPOSITION

TECHNICAL FIELD

This invention relates to a process for the preparation of 1,4-O-metallation products from the reaction of $\alpha,\beta$-unsaturated carbonyl compounds with hydrides of silicon, germanium, or tin in the presence of a heterogeneous noncomplexed rhodium-containing catalyst. It also relates to certain 1,4-O-metallation compositions wherein some specified R groups are perfluoroalkyl.

BACKGROUND AND SUMMARY OF THE INVENTION

The object of this invention is to produce a 1,4-O-metallation product of the general structure (C) by reacting an $\alpha,\beta$-unsaturated carbonyl compound (i.e., an ester, ketone or aldehyde) of the general structure (B) with a hydride of silicon, germanium, or tin of the general structure (A) in the presence of a heterogeneous noncomplexed rhodium-containing catalyst. The process involves the following single step reaction in which the carbon and oxygen positions are numbered.

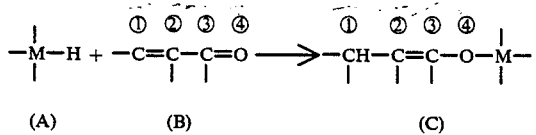

The reaction can be carried out in a solvent or neat, can be run with or without a polymerization inhibitor, can be run at mild reaction conditions (temperatures ranging from about 10° C. to about 75° C. and pressures from about atmospheric to about 20 psig), and yields a high purity product from which the catalyst can easily be separated for recovery or reuse.

The 1,4-O-metallation products, namely enol ethers of the form

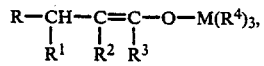

and ketene acetals of the form

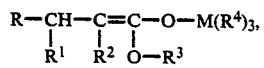

and of the form

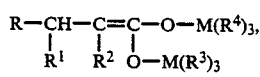

wherein M is silicon, germanium, or tin, are a useful class of compounds. They are reagents of choice in a wide range of reactions, including those which do not involve carbon-carbon bond formation, heterolytic reactions with carbon-carbon bond formation and pericyclic reactions. Some of these compounds are particularly useful as initiators in the manufacture of polymers for lacquers, oils or rubbers. See U.S. Pat. No. 4,417,034 issued to O. W. Webster on Nov. 22, 1983, and U.S. Pat. No. 4,508,880 issued to O. W. Webster on Apr. 2, 1985.

Compounds of the general structure

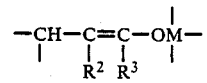

wherein M is silicon, germanium or tin and either $R^2$ or $R^3$ or both $R^2$ and $R^3$ are perfluoroalkyl and compounds of the general structure

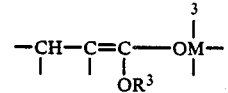

wherein M is silicon, germanium or tin, $R^3$ is perfluoroalkyl and no other R group is perfluoroalkyl are new compounds which can be synthesized by the process of this invention.

This invention is also useful for the production of 1,4-O-metallation polyfunctional initiators to be used in making higher molecular weight polymers than would be possible with 1,4-O-metallation products of the form shown above. The polyfunctional initiators are of the form

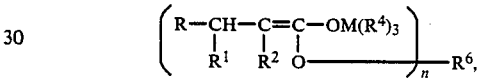

wherein M is silicon, germanium, or tin.

Representative of the 1,4-O-metallation products and processes for making them is the 1,4-O-silylated product, wherein M is silicon. In the past this type product has been synthesized by one of three methods—the silylation route, the enolate route, and the hydrosilylation route.

The silylation route is described by Rhone-Poulenc S.A. in its British Pat. No. 1,044,448. They describe the silylation of an organic compound in the presence of a nickel catalyst. The organic compound must contain an enolizable carbonyl group but be free from other functional groups which are reactive under the reaction conditions. The reaction is accompanied by the evolution of hydrogen, and may be represented as follows:

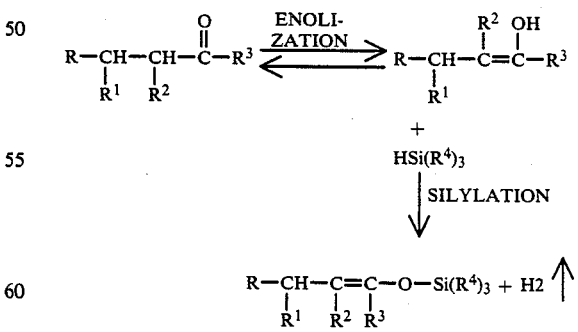

The reaction taught in the British Patent is limited to enolizable aldehydes and ketones. It also involves the evolution of hydrogen.

The enolate route is a three-step reaction which involves the following:
1. Generation of lithium diisopropylamide (LDA), 2. Reaction of the LDA in an organic solvent with the appropriate carbonyl compound to form the enolate, and
3. Reaction of the enolate with a halosilane to form the silylated product.

To isolate the silylated product prepared by the enolate route, filtration to remove salts, evaporation of solvent and distillation of the product are necessary. The process uses large quantities of flammable solvent and a pyrophoric material n butyl lithium to generate LDA. Also, the process suffers from low volumetric efficiencies (less than about 0.5 pound of product per gallon of raw materials) and it must be run at low temperatures (typically less than 0° C.).

The hydrosilylation route involves the reaction of silicon hydrides with $\alpha,\beta$-unsaturated carbonyl compounds. Reaction products of the hydrosilylation can be 1,2 $\alpha$-silylated products, 1,2 $\beta$-silylated products, 3,4-O-silylated products, or 1,4-O-silylated products.

MacKenzie, et al., describe the hydrosilylation route in their U.S. Pat. No. 2,721,873. That patent specifies the use of a silicon compound having at least one hydrogen attached to the silicon and an unsaturated organic compound containing the unsaturation in a non-benzenoid group to form an organo silicon compound. The silicon compounds utilized may be inorganic or organic. The unsaturated organic compounds include unsaturated hydrocarbons, aliphatic, carbocyclic, alicyclic and heterocyclic compounds including unsaturated alcohols, aldehydes, ketones, quinones, acids, acid anhydrides, esters, nitriles, or nitro compounds. The presence of added catalyst is nonessential, but MacKenzie, et al. say that they may be employed under certain conditions to facilitate reaction or increase yields. MacKenzie, et al. suggest that these catalysts may be selected from compounds and salts in the elements of groups IIIA, IVA, IB and IIB of the periodic system. Group VIII and some of their compounds are suggested as possibilities. Other types of catalysts such as peroxides are indicated and are cited as influencing the direction of addition which takes place.

Prior to this invention, 1,4 addition of silicon hydrides to $\alpha,\beta$-unsaturated carbonyl compounds has been shown to occur in the presence of a homogeneous or soluble catalyst such as tris(triphenylphosphine)rhodium(I) chloride. Since the catalyst is homogeneous, the product must be separated from the catalyst by distillation in order to recover the precious metal.

The process of this invention comprises reacting a hydride of silicon, germanium, or tin with $\alpha,\beta$-unsaturated esters, ketones or aldehydes in the presence of a heterogeneous noncomplexed rhodium-containing catalyst, that is, a solid catalyst in a gas or liquid system, to make a predominantly 1,4-O-metallation product. After the reaction is complete, the rhodium-containing catalyst can be easily removed by filtration to recover the precious metal. The crude product of this process, after filtration, can be distilled to isolate the 1,4-O-metallation product. In some cases distillation is not required for the product to be useful.

Polymerization inhibitors such as hydroquinone, tetramethyldiphenoquinone, phenothiazine and p-methoxyphenol can be used to retard polymerization of the unsaturated hydrocarbon. These are particularly advantageous when a gaseous hydride such as trimethylsilane is added to a slurry of the $\alpha,\beta$-unsaturated carbonyl compound and the heterogeneous rhodium catalyst.

While the process of this invention can be run neat, the reaction can be run in a solvent such as tetrahydrofuran (THF), ethyl acetate, or ethylene glycol dimethyl ether (glyme). For certain 1,4-O-metallation reactions, fewer impurities in the crude product result when a solvent is employed. Also, the choice of solvent can affect purity.

DETAILED DESCRIPTION OF THE INVENTION

The catalyst employed in this invention is a heterogeneous noncomplexed rhodium-containing catalyst. The degree of reduction of the rhodium can have a significant effect on the activity of the catalyst, with the most highly reduced rhodium exhibiting the least activity. It may be supported by a wide range of substrates including carbon, alumina and silica. The preferred support is carbon. The support chosen can have a significant effect on the rate of reaction.

The hydrides used in this invention are of the structure $H-M(R^4)_3$, wherein M is silicon, germanium, or tin, and $R^4$ can be chosen from such groups as hydrogen, halogens, branched or straight chained alkyl, aryl, alkoxy or benzyl groups including combinations of the groups. The preferred hydrides are the silicon hydrides, particularly alkylsilanes and principally triethylsilane, trimethylsilane, and methyldiethylsilane.

The $\alpha,\beta$-unsaturated carbonyl compounds of this invention are ketones, aldehydes, and esters of the following forms:

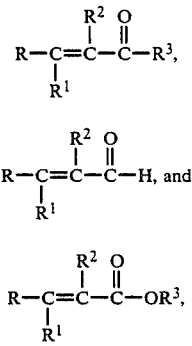

wherein R and $R^1$ can be independently hydrogen, fluoroalkyl or a hydrocarbyl radical which is an aliphatic, alicyclic, aromatic or mixed aliphatic(-)aromatic radical containing up to 20 carbon atoms, optionally containing one or more ether oxygen atoms within the aliphatic or alicyclic segments thereof and optionally containing one or more functional substituents that are unreactive under the conditions of the process. R and $R^1$ can be independently polymeric radicals containing at least 20 carbon atoms and optionally containing one or more oxygen atoms within aliphatic segments thereof and optionally containing one or more functional substituents that are unreactive under the conditions of this process.

$R^2$ and $R^3$ can be independently fluoroalkyl or hydrocarbyl radicals which are aliphatic, alicyclic, aromatic or mixed aliphatic-aromatic containing up to 20 carbon atoms, optionally containing one or more ether oxygen atoms within the aliphatic and alicyclic segments thereof and optionally containing one or more functional substituents that are unreactive under the conditions of this process. $R^2$ and $R^3$ can be independently polymeric radicals containing at least 20 carbon atoms and optionally containing one or more ether oxygen atoms within aliphatic segments thereof and optionally containing one or more functional substituents that are unreactive under the conditions of this process. $R^3$ can also be $(R^4)_3M$ or $R^5\text{-O-M}(R^4)_3$, where M is silicon, germanium, or tin; $R^5$ is a branched or straight chain alkyl or alkoxyalkyl having 1 to 20 carbon atoms; and $R^4$ is as defined in the case of the hydride.

New compositions are produced by the process of this invention when $R^3$ is perfluoroalkyl in above described ester; when $R^2$ is perfluoroalkyl in the above described aldehyde; or when either $R^2$ or $R^3$ or both are perfluoroalkyl in the above described ketone.

The $\alpha,\beta$-unsaturated esters may also be of the following general structure

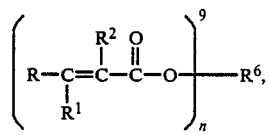

wherein "n" is a whole number of at least 2 and preferably from 2 to 4 and $R^6$ is a branched or straight chain alkyl, alkoxyalkyl, polyalkoxyalkyl, cycloalkyl or aryl group. R, $R^1$, and $R^2$ are as defined above. Esters of this form are reacted to produce 1,4-O-metallation polyfunctional compounds which can be used as polyfunctional initiators in making high molecular weight polymers.

The preferred $\alpha,\beta$-unsaturated compounds for making monofunctional initiators for polymer manufacture are the esters of the following form

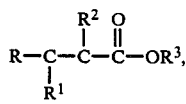

wherein R and $R^1$ are hydrogens, $R^2$ is $CH_3$ and $R^3$ is a branched or straight chain alkyl group from 1 to 8 carbon atoms; fluoroalkyl;

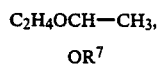

$C_2H_4N(R^7)_2$, wherein $R^7$ is a branched or straight chain alkyl group from 1 to 8 carbons; or $Si(R^4)_3$ or $C_2H_4Si(R^4)_3$, wherein $R^4$ is as defined above for the hydride.

The most preferred unsaturated esters for producing monofunctional initiators are methyl methacrylate ($R^3$ being $CH_3$), 2(1-ethoxyethoxy)ethyl methacrylate ($R^3$ being

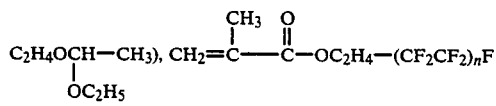

(n being 3 to 8), 2(1-butoxyethoxy)ethyl methacrylate ($R^3$ being

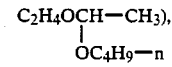

N,N-dimethylaminoethyl methacrylate ($R^3$ being $C_2H_4N(CH_3)_2$), and trialkylsilyl methacrylates ($R^3$ being $Si(C_2H_5)_2CH_3$, $Si(C_2H_5)_3$ or $Si(CH_3)_3$).

The preferred unsaturated esters for producing polyfunctional initiators are ethylene glycol dimethacrylate, butanediol dimethacrylate, trimethylolpropane trimethacrylate and pentaerythritol tetramethacrylate.

Where the hydride is liquid at ambient temperatures as in the case of triethylsilane, a preferred embodiment of the process comprises making a slurry of the heterogeneous rhodium catalyst and the hydride and then slowly adding the $\alpha,\beta$-unsaturated carbonyl compound to the slurry. Where the hydride is a gas at ambient temperatures as in the case of trimethylsilane, adding the hydride to a slurry of the catalyst and the $\alpha,\beta$-unsaturated carbonyl compound is preferred.

The $\alpha,\beta$-unsaturated carbonyl compound to hydride mole ratio preferably should be less than 1:1 but can be greater than 1:1. The preferred percent catalyst concentration (calculated as elemental rhodium) ranges from 0.01 to 0.15 mole percent of the hydride used.

The reaction of this invention is exothermic. Preferred temperatures range from 10° C. to 75° C. and preferred pressures range from atmospheric to 20 psig. The most preferred temperatures and pressures depend on the hydride and the $\alpha,\beta$-unsaturated carbonyl compound being reacted. The reaction preferably is carried out in an inert atmosphere since addition of oxygen to the system can cause excessive polymerization of the $\alpha,\beta$-unsaturated carbonyl compound.

Polymerization inhibitors may be used and may be preferred where the $\alpha,\beta$-unsaturated carbonyl compound is particularly sensitive to polymerization and where the hydride reactivity is low. For example, a polymerization inhibitor would be more preferable in a reaction between trimethylsilane and methyl methacrylate than in the faster reaction of triethylsilane and methyl methacrylate. Preferred polymerization inhibitors are hydroquinone, tetramethyldiphenoquinone phenothiazine and p-methoxyphenol.

Solvents are not required, but can be used. Preferred solvents are THF, ethyl acetate and glyme. Solvent addition can affect yield and purity of the desired 1,4-O-metallation product.

Other additives such as organic and inorganic acids and bases and salts can affect the rate of reaction. Also, catalyst impurities can affect the reaction.

EXAMPLES

The first ten examples are controls indicative of processes not claimed by this invention. The remaining examples are illustrative of the invention and are not intended to limit it in any way. NMR and gas chromatography were the standard laboratory procedures used to identify the product and determine yield and purity. In all examples the weight percent purity assumes that the gas chromatograph area percent for a compound equals the weight percent of that compound in the sample. The percent crude yield is calculated by means of the following equation:

$$\text{Percent Crude Yield} = \frac{\text{Weight of Filtrate} \times \text{Wt. \% Purity}}{\substack{\text{Theoretical Weight of} \\ \text{1,4-O—silylated Product} \\ \text{(i.e., 100\% yield assumed)}}}$$

EXAMPLES 1 AND 2

The first two examples employ a soluble catalyst, tris(triphenylphosphine)rhodium(I) chloride, in a reaction between methyl methacrylate (MMA) and triethylsilane (TES). In Example 1 a 10 mole percent excess of TES is used; in Example 2 a 50 mole percent excess of MMA is used. In both examples 0.2 gram of catalyst (about 0.1 mole percent) was added to a solution of TES and MMA in a clean, dry flask under a nitrogen atmosphere. In Example 1, 20 grams of MMA and 25.6 grams of TES were used. In each case the mixture was then heated to 55° to 65° C. and held at that temperature and agitated for 25 hours.

In Example 1 a mixture of compounds resulted. The crude yield of the 1,4-O-silylated product,

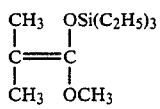

was about 30 percent with a purity of 40.4 weight percent. A similar product resulted in Example 2. In Example 2, however, the crude yield was about 65.5 percent and the purity was about 58.7 percent. Additionally, in Example 2 a 2.3 gram lump of polymeric material formed. In both Example 1 and Example 2 the tris(triphenylphosphine)rhodium(I) chloride catalyst is homogeneous and thus distillation is necessary to separate it from the reaction mixture to recover the rhodium. See Table I.

EXAMPLES 3 AND b 4

Examples 3 and 4 both use 1 gram of 5 percent platinum on carbon as the catalyst. In Example 3 a 10 percent excess of triethylsilane (25.6 grams or 0.22 mole) is reacted with 20 grams (0.2 mole) of methyl methacrylate in a clean, dry flask under a nitrogen atmosphere. In Example 4, 23.3 grams (0.2 mole) triethylsilene is reacted with a 50 percent excess of methyl methacrylate (30 grams or 0.3 mole) in a clean, dry flask under a nitrogen atmosphere. In both examples the triethylsilane and catalyst were charged to a clean, dry flask under a nitrogen atmosphere. The charge was heated to 60° to 65° C. and the methyl methacrylate was added dropwise over about 90 minutes. The mixture was maintained at 60° to 65° C. and agitated for a total of 31 hours and then filtered to remove the catalyst. In both Examples 3 and 4 the reaction product was principally the 1,2-$\beta$-silylated product of triethylsilane to methyl methacrylate. See Table I.

EXAMPLES 5 AND 6

Using the same procedure as in Examples 3 and 4 one gram of nickel/Kieselguhr catalyst was used in these examples. Example 5 was run with a 10 percent excess of triethylsilane (25.6 grams or 0.22 mole) and 20 grams (0.2 mole) of methyl methacrylate. Example 6 was run with a 50 percent excess of methyl methacrylate (30 grams or 0.3 mole) and 23.3 grams (0.2 mole) of triethylsilane. In both examples the methyl methacrylate was added dropwise over about 100 minutes and the charge was then maintained at 60° to 65° C. and agitated for about 26 hours. No reaction was observed in either case. Anhydrous nickel chloride in the amount of 0.1 gram was then added to the charge in each case. After an additional seven hours at 60° to 65° C. there was still no reaction. See Table I.

EXAMPLES 7, 8, 9 AND 10

Following the same procedure as in Examples 3 through 6 the catalyst in each of these examples was added to the triethylsilane and a 50 percent excess of methyl methacrylate was added dropwise over a 60 to 100 minute time period. In Example 7 one gram of 5 percent palladium on carbon was used as the catalyst. The charge was heated to 60° to 65° C. and maintained at that temperature and agitated for about 32 hours. In Example 8 the catalyst was one gram of 5 percent ruthenium on carbon. The mixture was heated to 60° to 65° C. and maintained at that temperature and agitated for about 18 hours. In Example 9 the catalyst was one gram cobalt on Kieselguhr. In this case the charge was agitated for about 18 hours at 20° to 25° C. and then was heated to 60° to 65° C. and agitated for about 12½ hours. In Example 10 the catalyst was one gram of 5 percent iridium on carbon. The charge was agitated at 20° to 25° C. for one hour and then the temperature was elevated to 60° to 65° C. and the charge was agitated for 22 hours. No reaction was observed in Example 9. In the other examples, principally 1,2-$\beta$-silylation product, substantial amounts of the starting materials and polymerized MMA resulted. See Table I.

TABLE I

Hydrosilylation of Methyl Methacrylate (MMA) with Triethylsilane (TES)

| Example | Catalyst | Temp. °C. | Time Hrs. | G.C. % Composition 1,2-$\beta$-Silylation | G.C. % Composition 1,4-O-Silylation | Comments |
|---|---|---|---|---|---|---|
| 1 | [$\phi_3$P]$_3$ RhCl | 55–60 | 25 | 16.4 | 40.4 | 10% excess TES<br>Some MMA polymerization |
| 2 | [$\phi_3$P]$_3$ RhCl | 55–60 | 25 | 1.6 | 58.7 | 50% excess MMA<br>Some MMA polymerization |
| 3 | 5% Pt/C | 60–65 | 31 | 61.8 | 0.3 | 10% excess TES |
| 4 | 5% Pt/C | 60–65 | 31 | 40.9 | 0.8 | 50% excess MMA |
| 5 | Ni/Kieselguhr +<br>NiCl$_2$ | 60–65<br>60–65 | 26<br>+7 | 0<br>0 | 0<br>0 | 10% excess TES<br>No detectable silylated products |
| 6 | Ni/Kieselguhr +<br>NiCl$_2$ | 60–65<br>60–65 | 26<br>+7 | 0<br>0 | 0<br>0 | 50% excess MMA<br>No detectable silylated products |
| 7 | 5% Pd/C | 60–65 | 23 | 8.5 | <0.1 | Further heating resulted<br>in MMA polymerization |
| 8 | 5% Ru/C | 60–65 | 18 | 11.0 | 0.3 | Considerable polymer formation |

TABLE I-continued

| | | | | G.C. % Composition | | |
|---|---|---|---|---|---|---|
| | | | | Hydrosilylation of Methyl Methacrylate (MMA) with Triethylsilane (TES) | | |
| Example | Catalyst | Temp. °C. | Time Hrs. | 1,2-β-Silylation | 1,4-O-Silylation | Comments |
| 9 | Co/Kieselguhr | 60–65 | 12 | 0 | 0 | No detectable silylated products |
| 10 | 5% Ir/C | 60–65 | 22 | 18.0 | 0.3 | Considerable polymer formation |

EXAMPLES 11 THROUGH 16

Using a procedure similar to that employed in Examples 3 through 10 the catalyst in each of these examples was added to the triethylsilane (TES) and the ester was added dropwise over a 60 to 75 minute time period. In Examples 11 through 14 a 50 percent excess of methyl methacrylate (MMA) was added. In Example 15 a 10 percent excess of MMA was added. In Examples 16 and 17 a 10 percent excess of 2(1-ethoxyethoxy)ethyl methacrylate (EEEM) (see U.S. Pat. No. 3,530,167) vacuum stripped of volatiles was used. When the ester was added in each of the examples, an exothermic reaction resulted. In Example 11 one gram of 5 percent rhodium on carbon was used as the catalyst. The reaction mixture was maintained at 60° to 65° C. and agitated after the addition of MMA for 1¼ hours. In Example 12 the catalyst was one gram of 5 percent rhodium on carbon. The temperature of the charge was maintained at 20° to 25° C. by means of an ice water bath and was agitated for 22 hours after the addition of MMA was complete. In Example 13, 0.1 gram of 5 percent rhodium on carbon was used and the temperature of the mixture was maintained at 20° to 25° C. while agitating for 24 hours following addition of the MMA. In Example 14, 0.1 gram of 5 percent rhodium on alumina was used and the mixture was maintained at 20° to 25° C. while agitating for 26 hours following addition of the MMA and then was heated to 60° to 65° C. for an additional four hours. In Example 15, 0.5 gram of 1 percent rhodium on carbon was used and the mixture was maintained at 30° to 35° C. while agitating for about four hours after the addition of MMA was complete. In Example 16, 0.5 gram of one percent rhodium on carbon was used and the mixture was maintained at 30° to 35° C. while agitating for about four hours following addition of the EEEM. In Example 17, 0.5 gram of 5 percent rhodium on carbon was used and the mixture was maintained at 30° to 35° C. while agitating for about 2½ hours after the addition of EEEM was complete.

In each example the catalyst was removed by filtration and the filtrate was analyzed. In each case a 1,4-O-silylated product resulted. In Examples 11 through 15 that product was of the form,

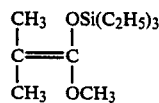

In Examples 16 and 17 the 1,4-O-silylated product was of the form,

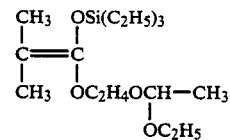

The approximate crude yield and purities are indicated in Table II.

TABLE II

| Example | Catalyst | Silane | α,β-Unsaturated Ester | 1,4-O-Silylation Crude Yield % Theory | Purity Wt. % |
|---|---|---|---|---|---|
| 11 | Rh/C | TES | MMA | 71 | 77 |
| 12 | Rh/C | TES | MMA | 52 | 47 |
| 13 | Rh/C | TES | MMA | 65 | 58 |
| 14 | Rh/Alumina | TES | MMA | 74 | 72 |
| 15 | Rh/C | TES | MMA | 85 | 87 |
| 16 | Rh/C | TES | EEEM | 94 | 93 |
| 17 | Rh/C | TES | EEEM | 93 | 94 |

EXAMPLES 18 THROUGH 21

In each of the following examples methyl methacrylate was reacted in the presence of a rhodium-on-carbon catalyst with silanes other than triethylsilane. The weight percent 1,4-O-silylated product (purity) in the filtrate from each of the reactions as well as the percent crude yield for each of the examples is set forth in Table III.

In Example 18 a 10 percent excess of methyl methacrylate (33 grams or 0.33 mole) and 0.2 gram of 5 percent rhodium on carbon were charged to a clean, dry 100-ml Hastelloy C shaker bomb. Then 22.3 grams (0.3 mole) trimethylsilane (TMS) was condensed into the charge. The charge was heated slowly to 35° to 45° C. and held at that temperature for two hours. After cooling the reaction mixture was filtered to remove the catalyst and the filtrate was analyzed. The 1,4-O-silylated product of this example has the following form:

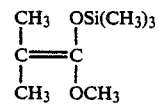

In Example 19, 16.6 grams (0.22 mole) trimethylsilane was added over about 4½ hours to a slurry of 0.5 gram 5 percent rhodium on carbon in 20 grams (0.2 mole) methyl methacrylate, 0.0041 gram hydroquinone and 20 ml dry tetrahydrofuran (THF). The reaction mixture was agitated in a four-necked glass flask at 35° to 39° C. for about 1½ hours. The system was maintained at about 3 psig during TMS addition by means of a six inch mercury pressure relief column attached to the flask and subsequently as needed by nitrogen addition. The catalyst was filtered off and the filtrate was analyzed.

The 1,4-O-silylated product was the same form as in Example 18.

In Example 20 a 50 percent excess of methyl methacrylate (30 grams or 0.3 mole) was added dropwise over 60 minutes to a mixture of 0.1 gram 5 percent rhodium-on-carbon catalyst and 27.3 grams (0.2 mole) phenyldimethylsilane in a clean, dry flask under a nitrogen atmosphere. After the addition was complete the temperature was maintained at 20° to 25° C. for 24 hours. The charge was filtered to remove the catalyst and the filtrate was analyzed. The 1,4-O-silylated product of this example had the form,

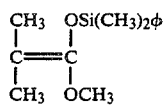

In Example 21 a 5 percent excess of methyl methacrylate (31.5 grams or 0.315 mole) was added dropwise over a 60 minute period to a slurry of 0.5 gram one percent rhodium on carbon in 30.7 grams (0.3 mole) of methyldiethylsilane (MDES) at 30° to 35° C. in a clean, dry flask under a nitrogen atmosphere. After the addition was complete, the charge was allowed to agitate at 30° to 35° C. for about 11½ hours. The charge was cooled and filtered to remove the catalyst and the filtrate was analyzed. The 1,4-O-silylated product of this example is of the form,

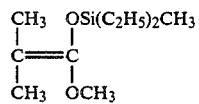

The 1,4-O-silylated product crude yields and purities for Examples 18 through 21 can be found in Table III which follows.

TABLE III

| Example | Catalyst | Silane | α,β-Unsaturated Ester | 1,4-O-silylation Crude Yield % Theory | Purity Wt. % |
|---|---|---|---|---|---|
| 18 | Rh/C | TMS | MMA | 45 | 49 |
| 19* | Rh/C | TMS | MMA | 70 | 51 |
| 20 | Rh/C | PDMS | MMA | 71 | 81 |
| 21 | Rh/C | MDES | MMA | 72 | 86 |

*Hydroquinone and THF added

EXAMPLES 22 AND 23

In Examples 22 and 23 methyl methacrylate was reacted in the presence of a rhodium-on-carbon catalyst with a chlorinated silicon hydride under a nitrogen atmosphere. The crude product was not analyzed by gas chromatography in either case. Instead, the reaction mixture was filtered to remove the catalyst and the filtrate was distilled. NMR was used to analyze the distillate.

In Example 22 a 50 percent excess of methyl methacrylate (30 grams or 0.3 mole), 0.5 gram 5 percent rhodium-on-carbon catalyst, and 18.9 grams (0.3 mole) distilled dimethylchlorosilane were charged to a 100-ml Hastelloy C shaker bomb and heated at 100° to 110° C. for one hour. The reaction mixture was filtered to remove the catalyst. Distillation of a 35.5 gram sample of the reaction mixture yielded 7.5 grams of a product with a boiling point of 34°-36° C. at 1.4 to 2.0 mm mercury. The NMR analysis of this product was consistent with the following structure:

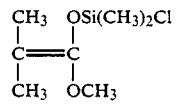

In Example 23 a 50 percent excess of methyl methacrylate (30 grams or 0.3 mole), 0.5 gram of 5 percent rhodium-on-carbon catalyst and 23 grams (0.2 mole) of distilled methyldichlorosilane were charged to a 100-ml Hastelloy C shaker bomb and heated to 85° to 95° C., held at that temperature for half an hour and then heated to 110° to 115° C. at which temperature the mixture was held for one hour. The reaction mixture was filtered to remove the catalyst. Distillation of a 40.2 gram sample of the reaction mixture yielded about 5.7 grams of a product with a boiling point of 33° to 37° C. at 1.5 to 1.6 mm mercury. NMR analysis of the sample indicated that it was a 1:1 molar mixture of 1,4-O-silylated and 1,2-α-silylated products of the respective forms:

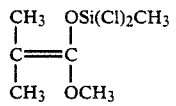

and

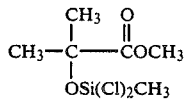

EXAMPLE 24

In this example 30.7 grams (0.3 mole) methyldiethylsilane and 0.5 gram of one percent rhodium on carbon were mixed in a dry, three-necked glass flask. The mixture was deoxygenated by bubbling nitrogen slowly through the mixture for one hour at approximately 25° C. A 10 percent excess of 2(1-butoxyethoxy)ethyl methacrylate (BEEM) (76 grams or 0.33 mole) was then added dropwise to the mixture over a 60 minute period at 30° to 35° C. The charge was agitated for six hours at 30° to 35° C. After filtering to remove the catalyst, the clear filtrate was analyzed. The 1,4-O-silylated product of this example had the form,

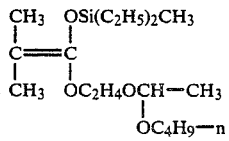

The purity (percent 1,4-O-silylated product in the filtrate) was 82 weight percent. The crude yield of the 1,4-O-silylated product was about 78 percent.

EXAMPLE 25

In this example 31.4 grams (0.2 mole) 2-dimethylaminoethyl methacrylate was added dropwise over about one hour to a slurry of 0.5 gram of 5 percent rhodium on carbon in 21.5 grams (0.21 mole) methyldiethylsilane and 25 ml dry ethyl acetate. The reaction mixture was agitated in a three-necked glass flask at 30° to 35° C. for about one hour. After catalyst filtration, the filtrate was analyzed. The 1,4-O-silylated compound formed was

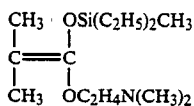

The purity was about 65 weight percent and the yield was about 87 percent of theory.

EXAMPLE 26

In this example 29.7 grams (0.15 mole) ethylene glycol dimethacrylate was added dropwise over a 60 minute period to a mixture of 0.5 gram 5 percent rhodium on carbon and 32.2 grams (0.315 mole) methyldiethylsilane at 30° to 35° C. After the addition was complete, the charge was agitated at 30° to 35° C. for four additional hours. After cooling the charge was filtered to remove the catalyst and the filtrate was analyzed. The 1,4-O-silylated product of this example had the form

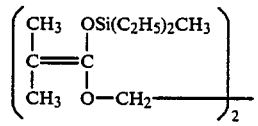

The purity (weight percent of the bis-1,4-O-silylated product in the filtrate) was about 68 weight percent. The yield of the product was about 65 percent of theory.

What is claimed is:

1. A composition of the formula

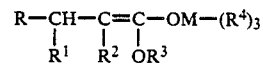

wherein M represents silicon, germanium or tin and $R^3$ represents a perfluoroalkyl group and R and $R^1$ are selected individually from the group consisting of hydrogen and alkyl, aryl, cycloalkyl and mixed alkyl-aryl radicals containing 1 to 20 carbon atoms, $R^2$ is selected from the group consisting of branched or straight chain alkyl radicals having 1 to 20 carbon atoms, fluoroalkyl, aryl, benzyl, cycloalkyl, substituted aminoalkyl, alkoxyalkyl, polyalkoxyalkyl, and phenoxyalkyl radicals; and $R^4$ is selected individually from the group consisting of hydrogen, halogens, and branched or straight chain alkyl, aryl, alkoxy, and benzyl radicals having from 1 to 20 carbon atoms.

2. The composition of claim 1 wherein M is silicon.

3. A composition of the formula

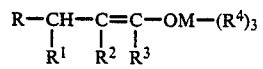

wherein M represents silicon, germanium or tin and $R^2$ and $R^3$ represents a perfluoroalkyl group and R and $R^1$ are selected individually from the group consisting of hydrogen and alkyl, aryl, cycloalkyl and mixed alkyl-aryl radicals containing 1 to 20 carbon atoms; and $R^4$ is selected individually from the group consisting of hydrogen, halogens, and branched or straight chain alkyl, aryl, alkoxy, and benzyl radicals having from 1 to 20 carbon atoms.

4. The composition of claim 3 wherein either $R^2$ or $R^3$ but not both represent a perfluoroalkyl group.

5. The composition of claim 3 wherein M is silicon.

6. The composition of claim 4 wherein M is silicon.

* * * * *